United States Patent [19]

Bohm et al.

[11] 4,005,143
[45] Jan. 25, 1977

[54] PROCESS FOR MANUFACTURING AROMATIC DIAMINES

[75] Inventors: Walter Bohm, Leverkusen; Helmuth Kritzler, Odenthal; Lutz Neumann, Cologne, all of Germany

[73] Assignee: Bayer Aktiengesellschaft, Leverkusen, Germany

[22] Filed: July 9, 1975

[21] Appl. No.: 594,417

[30] Foreign Application Priority Data

July 25, 1974 Germany .......................... 2435818

[52] U.S. Cl. ................ 260/575; 252/430; 260/580
[51] Int. Cl.² ................ C07C 93/26; C07C 85/11
[58] Field of Search ........................ 260/580, 575

[56] References Cited

UNITED STATES PATENTS

| 1,793,941 | 2/1931 | Laux | 260/580 |
|---|---|---|---|
| 2,164,154 | 6/1939 | Henke et al. | 260/580 |
| 2,292,879 | 8/1942 | Kise | 260/580 |
| 2,894,036 | 7/1959 | Graham | 260/580 |
| 3,232,989 | 2/1966 | Graham | 260/580 |

Primary Examiner—Arthur P. Demers
Attorney, Agent, or Firm—Burgess, Dinklage & Sprung

[57] ABSTRACT

Aromatic diamines having the formula

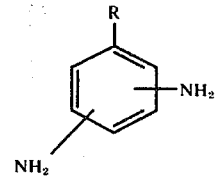

wherein
R is alkyl or alkoxy having up to 6 carbon atoms are prepared by treating dinitro compounds having the formula

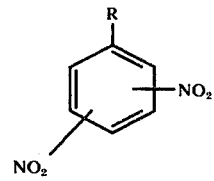

wherein
R is as previously defined, with hydrogen in the presence of one or more noble metals from the platinum or palladium groups as catalysts, optionally on catalyst supports, and in the presence of optionally substituted aniline as the solvent.

The catalyst is generally used in amounts of 0.0005 to 0.1% by weight based on the amount of dinitro compound employed.

7 Claims, No Drawings

PROCESS FOR MANUFACTURING AROMATIC DIAMINES

BACKGROUND

This invention relates to a process for the manufacture of aromatic diamines by catalytic hydrogenation of the corresponding dinitro compounds.

The catalytic reduction of dinitro compounds is a problem which has remained unsolved in many cases. The processes known in individual cases can in general not be applied with equal success to other starting compounds (German Pat. No. 948,784).

SUMMARY

It has now been found that aromatic diamines of the formula

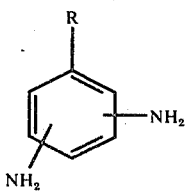

in which

R denotes a alkyl or alkoxy radical with up to 6 C atoms are obtained in good yield when dinitro compounds of the formula

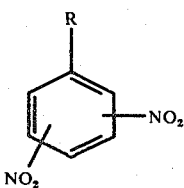

in which

R has the abovementioned meaning are treated with hydrogen in the presence of one or more noble metals of periods 5 and 6 of Group VIII of the Periodic Table (as shown on the end page of "Advanced Inorganic Chemistry," Cotton & Wilkinson, 1966, 2nd Edition, Interscience), as the catalyst and of optionally substituted aniline as the solvent.

DESCRIPTION

Possible $C_1$ to $C_6$ alkyl and alkoxy radicals are straight-chain and branched alkyl and alkoxy radicals; examples which may be mentioned are propyl, isopropyl, butyl, isobutyl, tert.-butyl and the isomeric pentyl and hexyl radicals; the range of meanings of the alkoxy groups corresponds to that of the abovementioned alkyl groups. Alkyl and alkoxy groups with up to 4, especially 2, carbon atoms are preferred; methyl and ethyl, and methoxy and ethoxy, should be mentioned particularly.

Preferred starting compounds for the process according to the invention are, in particular, dinitroanisole and dinitrophenetole.

Catalysts which can be used in the process according to the invention are one or more metals of periods 5 and 6 of group VIII of the Periodic Table defined herein i.e. osmium, iridium, platinum and ruthenium, rhodium and palladium, but are preferably platinum and palladium.

Of course, the abovementioned metals can also be carried on catalyst supports. Examples of possible catalyst supports are the carbonates and sulphates of the alkaline earth metals, for example barium carbonate, barium sulphate, calcium carbonate and calcium sulphate, as well as the argillaceous earth, aluminium oxide, silicon dioxide and silicic acids. The preferred catalyst support is charcoal, especially in the form of active charcoal; the preferred catalyst used is palladium on active charcoal.

Preferably, the amount of catalyst is 0.0005–0.1, most preferably 0.001–0.05 and especially 0.005–0.02% by weight of metal, based on the amount of dinitro compound employed. Preferably, the amount of supported catalyst (containing the above mentioned amount of catalyst therein) employed is 0.1–20, most preferably 0.2–10, and especially 0.5–5,% by weight, based on the amount of dinitroncompound employed.

Optionally substituted aniline can be used as the solvent in the process according to the invention. Preferably, aniline or an substituted aniline, such as $C_1$ to $C_4$ alkyl or $C_1$ to $C_4$ alkoxy as substituents are chosen, of which the melting point and/or boiling point are sufficiently below the melting point and/or boiling point of the diamine obtained as the reaction product to ensure simple separation by distillation and/or crystallisation. Preferably aniline, o-toluidine and m-toluidine are used, also for economic reasons.

In general it is desirable that the dinitro compound employed should be completely dissolved in the solvent. The solution of the dinitro compound is therefore advantageously prepared at the lowest temperature used in the reaction system, and an excess of the solvent is used. The magnitude of the excess of solvent has no effect on the process according to the invention; however, it is desirable to use an excess of 10 to 30%, preferably 15 to 25%, relative to the minimum amount of solvent required for solution under the abovementioned conditions.

The reaction pressure and reaction temperature are not material to the invention. The process according to the invention can be carried out even under normal pressure and at room temperature. However, it is preferably carried out at elevated temperature and elevated pressure because of the influence of temperature and pressure on the reaction rate.

Since the reaction takes place exothermically it is in general advisable to work in the temperature range of between 20° and 150° C, preferably 50° to 110° C; it is also possible to exceed the upper limit of the temperature range of 150° C but this in general tends to be disadvantageous. Because of the need to remove large amounts of heat, cooling difficulties arise, which can only be mastered at major expense, and the danger also arises that the reaction may get out of control and ultimately take place explosively.

In general, the reaction is carried out at a hydrogen pressure of up to 150 bars, preferably in the range of 5 – 30, especially 10 – 25, bars. Whilst the reaction time is also pressure-dependent, so that shorter reaction times are achieved as the hydrogen pressure is increased, problems relating to the apparatus in general arise at higher hydrogen pressure which again annul the advantage achieved.

In general, the reaction time depends on various factors so that it is not possible to make any general statement about its duration; the factors which influence it are the solvent system chosen and both the nature and the amount of the selected catalyst, the hydrogen pressure and the temperature. In general, the end of the reaction can be ascertained in accordance with known methods from the cessation of further hydrogen absorption; whether the starting compounds have been converted completely is particularly conveniently ascertained in discontinuously or continuously withdrawn samples, by means of known analytical methods, such as gas chromatography.

In general, the process according to the invention is carried out as follows:

The dinitro compound, the chosen solvent and the catalyst are introduced into the appropriate apparatus, the air is displaced with nitrogen and the mixture is constantly mixed well, for example by stirring, under the selected hydrogen pressure. The reaction mixture is brought to the selected reaction temperature by heating and the heating is terminated as soon as an appropriate autogenous temperature rise, due to the exothermic reaction, commences; thereafter, the reaction temperature is maintained by cooling. As stated above, it is advantageous that the nitro compound is in solution in the solvent during the reaction and that the reaction takes place in a homogenous phase, apart from the catalyst. The fact that a second, aqueous phase forms, as a result of the water of reaction produced, in the course of the reaction is in this respect immaterial.

In general, the catalyst is employed moist with water in order reliably to exclude catalysis of the explosive reaction of hydrogen with oxygen by the catalyst when charging and filling the apparatus with hydrogen. The small amounts of water introduced at the same time interfere as little as does the water of reaction which is formed.

After completion of the reaction, the reaction mixture is worked up in the usual manner. Suitably, after releasing the pressure and cooling, the catalyst is filtered off whilst still at an elevated temperature of about 30° to 80° C, preferably in the range from 40° to 60° C and in any case at a temperature at which — depending on the nature and amount of the selected solvent — none of the diamino compound obtained as the reaction product has as yet crystallised out.

The water of reaction produced can be separated from the organic phase in the usual manner, but it can also be removed together with the solvent when isolating the reaction product.

The diamine obtained as the reaction product can be isolated in the usual manner, for example by crystallisation or by distilling off the solvent; the reaction product can be purified further in the usual manner, for example by distillation or recrystallisation.

The process according to the invention advantageously permits the catalytic hydrogenation of aromatic dinitro compounds of the formula II. It was not to be expected that just by selection of the catalysts and solvents according to the invention better yields would be obtainable than with other customary catalysts, such as Raney nickel, and solvents, such as, for example, toluene, methanol and methanol-water mixtures, as is shown by the comparison examples.

Diaminoanisole and diaminophenetole can be obtained particularly advantageously in accordance with the process of the invention.

The compounds obtainable in accordance with the process of the invention are known intermediate products for the manufacture of dyestuffs and diisocyanates which can be used as starting compounds for the manufacture of plastics.

EXAMPLES

In each of the examples which follow, 86.4 g (0.436 mol) of 2,4-dinitroanisole was hydrogenated in a 700 ml stirred autoclave, in 300 ml of the solvent mentioned in Table I, at a temperature of about 80° C and a hydrogen pressure of between 5 and 10 bars. After completion of the reaction, complete conversion of the 2,4-dinitroanisole was tested for, and confirmed by, analysis by thin layer chromatography. After filtering off the catalyst, the solvent and the water of reaction formed were first distilled off under normal pressure and the crude 2,4-diaminoanisole was then fractionally distilled in vacuo; to obtain the pure product, the fraction passing over at between 160° and 170° C at 7 mm Hg was collected separately and characterised by its solidification point. Because of side reactions, a higher-boiling residue which was not analysed furthermore remained, and its amount is also indicated in Table I which follows.

Furthermore, Table I below shows the nature and amount of the catalyst used, both moist with water and converted to dry weight.

Table 1

| Example | Type | Catalyst g moist | g dry weight | Solvent | Reaction time, minutes | Pure Product g | % of theory | Solidification point °C | Residue, g |
|---|---|---|---|---|---|---|---|---|---|
| 1 * | 0.5% strength Pd/C | 23 | 9 | H$_2$O:CH$_3$OH (1:1) | 224 | 35.0 | 58.1 | 55.0 | 23.0 |
| 2 * | Raney nickel | 10 | 5 | CH$_3$OH | 76 | 33.0 | 54.9 | 57.5 | 22.9 |
| 3 * | 0.5% strength Pd/C | 23 | 9 | CH$_3$OH | 103 | 49.0 | 81.4 | 62.8 | 9.0 |
| 4 * | '' | 23 | 9 | Toluene | 87 | 51.5 | 85.6 | 61.4 | 9.5 |
| 5 | '' | 20.1 | 9 | Aniline | 103 | 50.4 | 83.7 | 62.8 | 7.0 |
| 6 | '' | 20.1 | 9 | o-Toluidine | 89 | 57.1 | 94.8 | 62.6 | 3.6 |
| 7 | 1.0% strength Pt/C | 9 | 4.5 | o-Toluidine | 94 | 51.8 | 86.1 | 62.1 | 4.1 |

(* Examples 1 to 4 are comparison examples)

EXAMPLE 8

67 g (0.316 mol) of 2,4-dinitrophenetole were hydrogenated, in a 700 ml stirred autoclave, in 330 ml of o-toluidine with 10 g of water-moist palladium catalyst (0.5% by weight of Pd on charcoal), corresponding to 4 g of dry catalyst, at a temperature of about 80° C and a hydrogen pressure of between 10 and 5 atmospheres gauge. After about 5¾ hours the reaction had ended; the catalyst was filtered off, the solvent and water of reaction were distilled under normal pressure and the residue was fractionally distilled in vacuo. 42.5 g (88.4% of theory) of 2,4-diaminophenetole, which showed a solidification point of 64.5° C, passed over in the boiling range of 144° – 170° C/3 mm Hg. 4.5 g of a higher-boiling residue remained.

EXAMPLE 9

112 g (0.529 mol) of 2,4-dinitrophenetole were hydrogenated, in a 700 ml stirred autoclave, in 300 ml of o-toluidine with 15 g of water-moist palladium catalyst (0.5% by weight of palladium on charcoal), corresponding to 6 g of dry catalyst, at a temperature of about 80° C and a hydrogen pressure of between 5 and 10 bars. After 3½ hours, the hydrogen absorption and the reaction had ended. After filtering off the catalyst, the solvent and the water of reaction formed were distilled off under normal pressure and the residue which remained was then fractionally distilled in vacuo. 71.7 g (89.3% of theory) of 2,4-diaminophenetole of solidification point 64.2° C were obtained in the boiling range of 150° – 180° C/5 mm Hg. 4.5 g of a higher-boiling residue remained.

EXAMPLE 10

100 g (0.472 mol) of 2,4-dinitrophenetole were hydrogenated, in a 700 ml stirred autoclave, in 300 ml of o-toluidine with 12 g of water-moist palladium catalyst (1.0% by weight of palladium on active charcoal), corresponding to 4.8 g of dry catalyst, at about 80° C and a hydrogen pressure of between 5 and 10 bars. After about 2¾ hours, the hydrogen absorption and the reaction had ended. The catalyst was filtered off and the solvent and water of reaction were distilled off under normal pressure. 69.8 g (97.3% of theory) of crude 2,4-diaminophenetole of solidification point 63.5° C were obtained. The compound purified by distillation under reduced pressure had a solidification point of 64.2° C.

EXAMPLE 11

1.355 kg (6.84 k mol) of 2,4-dinitroanisole are hydrogenated with hydrogen (10 bars), in a pressure apparatus, in 8,000 l of o-toluidine in the presence of 19.3 kg of dry Pd/C catalyst (0.5% Pd) at 80° C. After filtering off the catalyst, the water of reaction and the solvent are distilled off. 883.3 kg (= 93.5% of theory, relative to 2,4-dinitroanisole) of crude 2,4-diaminoanisole remain. The subsequent vacuum distillation of the crude product gives 757.9 kg (80.3% of theory, based on 2,4-dinitroanisole) of pure 2,4-diaminoanisole.

What is claimed is:

1. Process for preparing an aromatic diamine having the formula

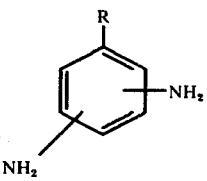

wherein
R is an alkyl or alkoxy group having up to 6 carbon atoms which comprises contacting in the presence of a solvent selected from the group consisting of aniline, O-toluidine and m-toluidine a dinitro compound of the formula

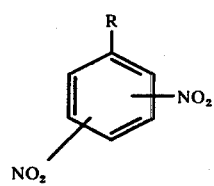

wherein
R is as defined above with hydrogen in the presence of a catalyst containing at least one metal of period 5 or 6 of Group VII of the Periodic Table, said catalyst being present in an amount of 0.0005 to 0.1% by weight metal, based upon the amount of dinitro compound being reacted.

2. Process of claim 1 wherein the metal is palladium.

3. Process of claim 1 wherein the metal is palladium and said palladium is deposited on active charcoal.

4. Process of claim 1 wherein the amount of catalyst is 0.005 to 0.02% by weight of nobel metal based on the amount of dinitro compound employed.

5. Process of claim 1 wherein the solvent is selected from the group of, O-toluidine and m-toluidine.

6. Process according to claim 1 wherein the solvent is O-toluidine.

7. Process according to claim 1 wherein the solvent is m-toluidine.

* * * * *